(12) United States Patent
Darbouret et al.

(10) Patent No.: US 7,981,621 B2
(45) Date of Patent: Jul. 19, 2011

(54) IN VITRO METHOD FOR DIAGNOSING AND MONITORING RENAL CELL CARCINOMA (RCC) USING MMP-7 AS HUMORAL BIOMARKER FOR RCC

(75) Inventors: Bruno Darbouret, Tresques (FR); Gaiané Sarkissian, Nimes (FR)

(73) Assignee: Cezanne S.A.S., Nimes Cedex (FR)

( * ) Notice: Subject to any disclaimer, the term of this patent is extended or adjusted under 35 U.S.C. 154(b) by 0 days.

(21) Appl. No.: 12/064,655

(22) PCT Filed: Aug. 21, 2006

(86) PCT No.: PCT/EP2006/008212
§ 371 (c)(1),
(2), (4) Date: Feb. 25, 2008

(87) PCT Pub. No.: WO2007/022940
PCT Pub. Date: Mar. 1, 2007

(65) Prior Publication Data
US 2008/0254483 A1 Oct. 16, 2008

(30) Foreign Application Priority Data
Aug. 26, 2005 (EP) .................................. 05291783

(51) Int. Cl.
*G01N 33/53* (2006.01)
(52) U.S. Cl. ...................................................... 435/7.1
(58) Field of Classification Search .................. None
See application file for complete search history.

(56) References Cited

U.S. PATENT DOCUMENTS

| 2004/0029200 A1 | 2/2004 | Weimbs |
| 2004/0253637 A1 | 12/2004 | Buechler et al. |

FOREIGN PATENT DOCUMENTS

| JP | 08-217800 | 8/1996 |
| JP | 08217800 | * 8/1996 |
| JP | 10287700 | 10/1998 |
| WO | 02082076 | 10/2002 |

OTHER PUBLICATIONS

Sumi et al (Oncology Reports, 2003, 10: 567-570).*
Ohuchi et al (Clinica Chimica Acta, 1996, 244: 181-198).*
Sherief et al (The Journal of Urology, Apr. 2003, 169: 1530-1534).*
Yasunori et al (JP 08217800; Aug. 27, 1996).*
Boer, J.M., Huber W.K., Sultmann H. Identification and classification of differentially expressed genes in renal cell carcinoma by expression profiling on a global human 31,500-element cDNA array. Genome Research 2001 11: 1861-1870.

European Office Action for EP Application No. 06 791 599.1-1223 issued on Oct. 3, 2009.
International Search Report for PCT/EP2006/008212 filed Aug. 21, 2006.
Kallakury et al., "Increased expression of matrilysin (MMP7) and stromelysin (MMP3, MMP10, MMP11) proteins as predictors of survival in RCCs." Modern Pathology, vol. 16(1), Jan. 2003, p. 155A, Abstract 707.
Lein et al., "Matrix-metalloproteinases and their inhibitors in plasma and tumor tissue of patients with renal cell carcinoma", International Journal of Cancer, Mar. 15, 2000, vol. 85(6), 801-804.
Sumi et al., "Expression of matrix metalloproteinases 7 and 2 in human renal cell carcinoma", Oncology Reports, May-Jun. 2003, vol. 10(3), 567-570.
Struckmann et al., "MMP and TIMP expression are relevant for renal cancer progression", Pathology Research and Practice, vol. 199(4), 2003, Abstract 297.
Wilson et al., "Matrilysin: An Epithelial Matrix Metalloproteinase with Potentially Novel Functions", Int. J. Biochem. Cell Biol., vol. 28(2) 123-136, 1996.
Van Wart et al., "The cysteine switch: A principle of regulation of metalloproteinase activity with potential applicability to the entire matrix metalloproteinase gene family", Proc. Natl. Acad. Sc. USA, vol. 87, Jul. 1990, 5578-5582.
Imai et al., "Matrix Metalloproteinase 7 (Matrilysin) from Human Rectal Carcinoma Cells", The Journal of Biological Chemistry, vol. 270(12), Mar. 24, 1995, 6691-6697.
Sherief et al., "Matrix Metalloproteinase Activity in Urine of Patients with Renal Cell Carcinoma Leads to Degradation of Extracellular Matrix Proteins: Possible Use as a Screening Assay", The Journal of Urology, vol. 169, Apr. 2003, 1530-1534.
Shimazui et al., "Complex Cadherin Expression in Renal Cell Carcinoma", Cancer Research 56, Jul. 15, 1996, 3234-3237.
Vogelzang et al., "Kidney cancer", The Lancet 1998, vol. 352, Nov. 21, 1998, 1691-96.
Nagase et al., "Matrix Metalloproteinases", The Journal of Biological Chemistry, vol. 274(31), Jul. 30, 1999, 21491-21494.
Yamamoto et al., "Expression of Matrix Metalloproteinases and Tissue Inhibitors of Metalloproteinases in Human Pancreatic Adenocarcinomas: Clinicopathologic and Prognostic Significance of Matrilysis Expression", Journal of Clinical Oncology, vol. 19(4), Feb. 15, 2001, 1118-1127.
Reynolds et al., "The functional balance of metalloproteinases and inhibitors in tissue degradation: relevance to oral pathologies", J.R. Coll. Surg. Edinb., vol. 42, Jun. 1997, 154-160.

(Continued)

*Primary Examiner* — Sean E Aeder
(74) *Attorney, Agent, or Firm* — Heslin Rothenberg Farley & Mesiti P.C.

(57) ABSTRACT

The present invention relates to the use of matrix metalloproteinase 7 (MMP-7) and/or its precursors and fragments with MMP-7 immunoreactivity, or of circulating anti-MMP-7 antibodies, as humoral biomarkers in diagnostic in vitro methods for the detection, early detection, monitoring and/or prognosis of renal cell carcinoma (RCC) in human patients.

6 Claims, 6 Drawing Sheets

OTHER PUBLICATIONS

Ohuchi et al., "A one-step sandwich enzyme immunoassay for human matrix metalloproteinase 7 (matrilysin) using monoclonal antibodies", Clinica Chimica Acta 244 (1996) 181-198.

Flickinger et al., "Post-obstruction rat sperm autoantigens identified by two-dimensional gel electrophoresis and western blotting", Journal of Reproductive Immunology 43 (1999) 35-53.

Korneeva et al., "Serum antibodies to the 27-kd heat shock protein in women with gynecologic cancers", American Journal of Obstetrics and Gynecology, vol. 183(1), 18-21, 2000.

Mathis, Gerard, "Rate Earth Cryptates and Homogeneous Fluoroimmunoassays with Human Sera", Clinical Chemistry, vol. 39(9), 1993, 1953-1958.

Birkedal-Hansen et al., "Matrix Metalloproteinases: A Review", Critical Reviews in Oral Biology and Medicine, 4(2): 1993, 197-250.

Shiomi et al., "MT1-MMP and MMP-7 in invasion and metastasis of human cancers", Cancer and Metastasis Reviews 22, 2003, 145-152.

Rak et al., "Consequences of angiogenesis for tumor progression, metastasis and cancer therapy", Anti-Cancer Drugs 1995, vol. 6, 3-18.

Senota et al., "Relation of matrilysis messenger RNA expression with invasive activity in human gastric cancer", Clinical & Experimental Metastasis, vol. 16(4), 1998, 313-321.

McDonnell et al., "Expression and Localization of the Matrix Metalloproteinase Pump-1 (MMP-7) in Human Gastric and Colon Carcinomas", Molecular Carcinogenesis 4, 1991, 527-533.

Tanimoto et al., "The Matrix Metalloprotease Pump-1 (MMP-7, Matrilysin): A Candidate Marker/Target for Ovarian Cancer Detection and Treatment", Tumor Biology 1999, 20, 88-98.

Hofmann et al., "Prognostic Value of Urokinase Plasminogen Activator and Plasminogen Activator Inhibitor-1 in Renal Cell Cancer", The Journal of Urology, vol. 155, Mar. 1996, 858-862.

Kugler et al., "Expression of Metalloproteinase 2 and 9 and their Inhibitors in Renal Cell Carcinoma", The Journal of Urology, vol. 160, Nov. 1998, 1914-1918.

Sires et al., "Matrilysin is Much More Efficient than Other Matrix Metalloproteinases in the Proteolytic Inactivation of alpha-1 Antitrypsin", Biochemical and Biophysical Research Communications, vol. 204(2), Oct. 28, 1994, 613-620.

Murphy et al., "Matrix metalloproteinase degradation of elastin, type IV collagen and proteoglycan", Biochem Journal 1991, vol. 277, 277-279.

Adachi et al., "Clinicopathologic and Prognostic Significance of Matrilysin Expression at the Invasive Front in Human Colorectal Cancers", Int. J. Cancer, vol. 95, 2001, 290-294.

Yoshimoto et al., "Expression of MMP-7(PUMP-1) mRNA in Human Colorectal Cancers", Int. J. Cancer, vol. 54, 1993, 614-618.

Kotera et al., "Humoral Immunity against a Tandem Repeat Epitope of Human Mucin MUC-1 in Sera from Breast, Pancreatic, and Colon Cancer Patients", Cancer Research 54, Jun. 1, 1994, 2856-2860.

Unwin et al., "Urological malignancies and the proteomic-genomic interface", Electrophoresis 1999, vol. 20, 3629-3637.

Blay et al., "Serum Level of Interleuken 6 as a Prognosis Factor in Metastatic Renal Cell Carcinoma", Cancer Research, vol. 52, Jun. 15, 1992, 3317-3322.

Kleiner et al., "Matrix metalloproteinases and metastasis", Cancer Chemotherapy Pharmacol, 1999, 43, S42-S51.

* cited by examiner

US 7,981,621 B2

IN VITRO METHOD FOR DIAGNOSING AND MONITORING RENAL CELL CARCINOMA (RCC) USING MMP-7 AS HUMORAL BIOMARKER FOR RCC

CROSS REFERENCE TO RELATED APPLICATIONS

This application is a 371 filing of PCT International application no. PCT/EP2006/008212 filed Aug. 21, 2006 and published as WO 2007/022940 on Mar. 1, 2007 which claims the priority of European application no. 05291783.8 filed Aug. 26, 2005. The disclosures of these applications and all other patents, published applications and other references cited herein are hereby incorporated by reference in their entirety.

FIELD OF THE INVENTION

The present invention relates to a highly sensitive and specific in vitro method for the diagnosis of renal cell carcinoma (RCC) based on the new finding that a selected metalloproteinase, namely MMP-7, and/or its physiological precursor, pro-MMP-7, are elevated in body fluids, especially serum or plasma, of RCC patients. The present invention also relates to a specific ligand assay method for the detection of MMP-7 in a body fluid sample, i.e. the use of MMP-7 as humoral biomarker for RCC.

BACKGROUND OF THE INVENTION

Renal cell carcinoma (RCC) is the third most common malignancy of the urinary tract after prostate and bladder cancer. It is a cancer which is particularly difficult to diagnose. Indeed, RCC patients frequently have non-specific symptoms or are completely asymptomatic until a relatively advanced state is reached. Consequently, at the time of diagnosis, 15 to 25 percent of kidney cancer patients already have metastatic RCC. Once metastatic disease develops, the prognosis for long-term survival is poor.

Today, RCC normally is incidentally detected by abdominal ultrasound (US) and computed tomography (CT). It is occasionally suggested by a radioisotope bone or renal perfusion scan. However, these techniques are time consuming and expensive.

A number of efforts are currently performed to characterize RCC using molecular biological, cytogenetic, immunohistochemical as well as proteome-based techniques. In this context, many markers have been evaluated for their potential use as diagnostic or prognostic factors. However, as yet none of them has been validated in vigorous trials. The current state of the matter can be summarized as follows:

Interleukin 6 and its receptor might play a role in tumor proliferation as well as in certain symptom signs associated with metastatic renal cancer (Blay J Y et al., Cancer Res. (1992) 52, 3317-22).

FGF (Fibroblast Growth Factor), an angiogenic factor, may serve as potential prognostic marker of disease progression (Rak J W et al, Anticancer Drugs, (1995) 6, 3-18).

Plasminogen activator inhibitor-1, a specific inhibitor of urokinase, was reported as a prognostic factor in predicting early relapse of renal cell carcinoma. High and low risk groups for disease-free survival can be discriminated by plasminogen activator inhibitor-1 antigen content in the tumor tissue (Hofmann R et al, J. Urol. (1996) 155, 858-62).

Recent studies have described that expression of E-cadherin, which plays a major role in cell-cell adhesion of normal epithelium, is decreased in renal cancer. Its rate may be correlated with tumor aggressiveness (Shimazui T, Cancer Res. (1996) 56, 3234-7).

WO 02/082076 relates to identification of tumor markers which are immunogenic in RCC patients. The authors reported that these proteins are presented at the surface of the tumor cell and therefore are not circulating. The authors describe an immunoassay to detect the presence of circulating antibodies specific to these tumor marker proteins in the serum of an individual. Therefore, the immunoassay is not based on the direct detection of RCC markers in the circulation but on an indirect detection of (circulating) autoantibodies raised against RCC tumor marker proteins present in patients' tissue. Matrix metalloproteinases or antibodies against matrix metalloproteinases are not mentioned.

There is still a need for additional tumor markers for the detection and follow-up of renal cell carcinoma, especially for humoral tumor markers which can be detected in blood samples and serum or plasma samples respectively and which, therefore, can be included in the list of biomarkers determined in routine patient health screening. If it were possible to early diagnose renal tumors, this would have a very high impact on improving the outcome of RCC. The availability of an effective diagnostic assay would make it possible to screen routinely especially high risk populations (i.e. Von Hippel-Lindau, Hemodialysis, transplanted or immunodepressed patients, (N. J. Vogelzang, (1998) The Lancet, 352, 1691-1696)) and to detect asymptomatic tumor. A sensitive humoral renal cell carcinoma marker test would also have high value for detecting tumor recurrence in patients with renal cell carcinoma after total or partial nephrectomy. Such a marker will allow completing the evaluation of the extension of the disease. It may help to limit the use of invasive examination and to adapt therapeutics earlier. Such humoral marker will facilitate the monitoring of tumors during the treatment and allow a better prediction of therapeutic responses and prognosis.

SUMMARY OF THE INVENTION

Toward these ends, and others, it is an object of the present invention to provide an in vitro method for the diagnosis of RCC on the basis of a humoral biomarker directly measurable in body fluids of patients, more specially blood, serum and plasma.

According to present invention, and based on the clinical determinations and tests described herein, a diagnosis, prognosis and monitoring of renal cell carcinoma (RCC) is made possible by the use of matrix metalloproteinase 7 (MMP-7) and/or its precursors and fragments with MMP-7 immunoreactivity, or of circulating anti-MMP-7 antibodies, as humoral biomarkers for the detection, early detection, monitoring and/or prognosis of renal cell carcinoma (RCC) in human patients.

DETAILED DESCRIPTION OF THE INVENTION

Figure 1:
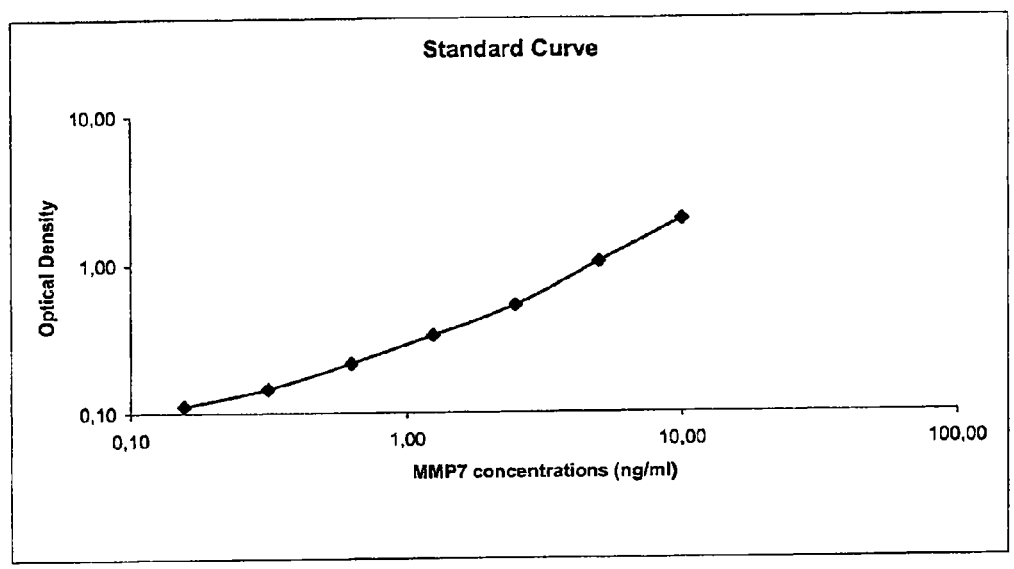
FIG. 1 is a standard curve for the measurement of MMP-7 levels in serum of patients with renal cell carcinoma (RCC) with an enzyme-linked immunoassay as described in the experimental section.

In the context of the present application, terms as "diagnosis" or "diagnostic", unless defined more detailed otherwise or in a narrower sense, usually are used as generic terms intended to cover not only diagnosis in the narrow sense of detection and identification of a disease or condition, but also monitoring the course of an already diagnosed disease, including the therapy accompanying assessment of the success of therapeutic measures, and the prognosis for the expected course of a disease and the survival of a patient.

The term "humoral biomarker" is used to describe biomarkers, or an immunoreactivity associated with such biomarkers, which can be determined in body fluids, especially in the circulation, as opposed to tissue biomarkers which require tissue material, usually obtainable only by biopsy or puncture, for their determination.

In said claims, the term "level" means amount or concentration, which can be given in exact numbers for mass per volume, but also as arbitrary units defined by the calibration of the assay used for the determination.

MMP-7 and pro-MMP-7 are peptidic, metal containing biomolecules of known structures and amino acid sequences. MMP-7 displays enzymatic activity and belongs to a group of functionally and structurally related molecules termed "matrix metallo-proteinases" which, in addition to trivial names, are characterized by systematic abbreviations consisting of the letters MMP and a number (i.e. MMP-xx). In humans, 16 members of this family have been identified (Kleiner et al., (1999) Cancer Chemother Pharmacol., 1999; 43 Suppl: S42-15), and if non-human species are considered as well, the number of M_MPs is still higher (a minireview by Hideaki Nagase et al. (1999), J. Biol. Chem. 274, pp. 21491-21494 lists 20 family members). MMPs in general and MMP-7 in particular are discussed next.

Matrix Metalloproteinases

Matrix metalloproteinases (MMPs), also called matrixins, constitute a family of zinc and calcium dependent endopeptidases that function in the breakdown of extracellular matrix (ECM).

The MMPs have been implicated in a wide variety of normal physiological processes including bone and tissue remodelling, uterine resorption, trophoblast implantation, angiogenesis, embryonic development and normal wound healing (Kleiner and Stetler-Stevenson, Cancer Chemother Pharmacol. (1999) 43 Suppl:S42-51; Nagase, H. et al (1999) J. Biol. Chem. 274, 2191). When present in excess, they are also thought to participate in the accelerated breakdown of ECM that is associated with a number of diseases including periodontitis (Reynolds and Meikle, J R Coll Surg Edinb. (1997) 42(3):154-60), arthritis, atherosclerosis, tissue ulcerations, tumor cell invasion, and metastasis (Birkedal-Hansen et al., Crit Rev Oral Biol Med. (1993) 4(2):197-250).

Matrix metalloproteases are known to play an important role in tumor invasion by mediating degradation of extracellular matrix (Shiomi T et al, Cancer Metastasis Rev. (2003) 22(2-3), 145-152).

Metalloproteinases of the types MMP-2 and MMP-9 were reported to be elevated in RCC tumor tissue, and their expression levels were suggested to correlate with tumor aggressiveness (Kugler et al, J. Urol. 1998 November; 160(5):1914-8).

Lein M et al found that MMP-9 was elevated in tumor tissue of patients with RCC, whereas MMP-2 was not different between tumor tissue and normal counterparts (Int J. Cancer. 2000 Mar. 15; 85(6):801-4).

Sherief et al described that it is possible to detect in urine from patients with renal cell carcinoma an elevated enzyme activity of matrix metalloproteinases, which leads to the degradation of normally excreted extracellular matrix (ECM) proteins. Decreased urinary ECM proteins were analysed by SDS-PAGE followed by immunoblotting with antibodies against three types of ECM proteins. Enzyme matrix metalloproteinase activity was measured using fluorescein conjugated collagen IV substrate (Sherief M H, J. Urol. (2003) 169(4), 1530-4).

In an enzymatic determination, MMPs are not directly measured. Since in such measurements only an enzymatic activity is determined, they do not allow it to draw reliable conclusions regarding the type of MMP(s) responsible for the observed enzymatic activity.

Similarly, in US 2004/0029200 it was reported a method for diagnosing RCC by detecting in urine of patients extracellular matrix protein resulting from proteolytic degradation by enzyme activity of metalloproteinase. It is mentioned that MMPs include MMP-2, MMP-3 and MMP-9. Interestingly, the authors specified that increased activity of metalloproteinases does not necessarily mean that the amount of a metalloproteinase must be increased. Therefore, it has been shown that the amounts of MMP-2 and MMP-9 are not consistently increased in urine of RCC patients compared to controls.

MMP-7

MMP-7, the metalloproteinase determined in the method of the present invention, structurally is one of the smallest of all MMPs, consisting of two domains, a pro-domain and a catalytic domain.

MMP-7 is also known as Matrilysin, Pump-1, protease Uterine metalloproteinase, Matrix metalloproteinase-7, and Matrin (Swiss-Prot accession number: P09237, EC 3.4.24.2).

MMP-7 is secreted as a precursor form (pro-MMP-7) that is activated by 4-aminophenylmercuric acetate (APMA) and trypsin in a stepwise manner (Imai K et al, J Biol Chem (1995) 270, 6691-6697). Activation of the proenzyme involves a proteolytic removal of the N-terminal pro-region containing the cysteine switch motif conserved in MMPs (Van Wart, H. E. and H. Birkedal-Hansen (1990) Proc. Natl. Acad. Sci. USA, 87, 5578).

MMP-7 can cleave a broad range of extracellular matrix macromolecules such as fibronectin, laminin, proteoglycan, elastin, gelatin and type IV collagen as well as $\alpha_1$-antitrypsin (Murphy G et al, Biochem J (1991) 277, 277-279; Sires U et al, Biochem Biophys Res Commun, (1994) 204, 613-620).

MMP-7 is expressed in epithelial cells of normal and diseased tissues (Wilson, C. L. and L. M. Matrisian (1996) Int. J. Biochem. Cell Biol. 28, 123).

MMP-7 is frequently overexpressed in various cancers such as gastrointestinal (McDonnell S et al, Mol Carcinog. (1991), 4(6), 527-33; Senota A, Clin Exp Metastasis. (1998) 16(4), 313-21), colorectal (Yoshimoto Met al, Int J. Cancer. (1993) 54(4), 614-8; Adachi Y, Int J. Cancer. (2001) 95(5), 290-4), ovarian (Tanimoto H, Tumor Biol. (1999) 20(2), 88-98), pancreatic (Yamamoto H et al, Journal of Clinical Oncology, (2001) 19(4), 1118-1127).

Increased expression of MMP-7 was also observed in high grade RCC tumors (Sumi T et al, Oncol Rep. (2003) 10(3), 567-70).

However, mRNA overexpression is determined in tissue extracts, e.g. tumor tissue extracts, and it is well documented that mRNA overexpression in many cases does not correlate with increased serum levels of corresponding proteins, e.g. in serum of cancer patients.

In fact, it has been reported that pro-MMP-7 levels in the sera from patients with colorectal cancer showed no significant difference from those of normal sera although pro-MMP-7 was overexpressed in colon adenocarcinoma cells (Ohuchi E et al, Clin Chim Acta. (1996) 244(2), 181-98).

Increased serum levels of MMP-7 and pro-MMP-7 were reported in rectal and prostatic cancer patients (JP10287700 and JP8217800).

To date, none of the studies described above have suggested that MMP-7 or pro-MMP-7 levels may be used as humoral markers for early detection or detection of RCC.

Similarly, none of the studies suggests that MMP-7 and/or pro-MMP-7 levels in body fluids may be used to monitor RCC treatment efficiency and RCC evolution.

Indeed, the inventors have shown for the first time that a significant number of RCC patients have increased circulating MMP-7 and/or pro-MMP-7 immunoreactivity levels. In this way, MMP-7 and/or pro-MMP-7 can be used as positive predictive parameter for RCC detection as high, statistically significant RCC probability is found for patients having increased MMP-7 and/or pro-MMP-7 levels.

Therefore, MMP-7 and/or pro-MMP-7 represent valuable markers for RCC diagnosis of high risk populations, for the follow-up in the management of RCC patients, for monitoring the evolution of RCC and as well as for measuring the efficiency of cancer treatment.

The present invention provides a method of diagnosing or detecting RCC in a cancer patient comprising periodically analyzing a sample of body fluid from such patient for MMP-7 and/or pro-MMP-7; comparing the MMP-7 and/or pro-MMP-7 levels in such body fluid with levels of MMP-7 and/or pro-MMP-7 in preferably the same body fluid type of a normal human control, wherein an increase in MMP-7 and/or pro-MMP-7 levels in the patient versus the normal human control is associated with RCC.

The inventors identified MMP-7 and pro-MMP-7 by using techniques which combine conventional proteome analysis with serological screening allowing the identification of immunogenic components in RCC (Unwin et al., Electrophoresis (1999) 20, 3629).

MMP-7 and pro-MMP-7 of the present invention first have been identified by two-dimensional gel electrophoresis of protein extracts from an RCC cell line and subsequent detection by immunoblotting with RCC patients' sera. The immunostained protein spot was excised from a duplicate gel, subjected to gel digestion and analyzed by mass spectrometry. With differential analysis of sera from patients versus healthy volunteers the above mentioned protein was identified as tumor marker in RCC patients (Flickinger C et al, J. Reprod. Immunol. (1999) 43, 35-53).

MMP-7 and/or pro-MMP-7 can be used as humoral biomarkers in a variety of diagnostic applications as they are exemplified below:

Because of the nature of the immune response, it is likely that autoantibodies can be elicited by a very small amount of circulating tumor marker protein, and indirect methods which rely on detecting the immune response to tumor markers may consequently be an alternative to their direct determination, and may even be more sensitive than methods for the direct measurement of tumor markers in body fluids. Assay methods based on the detection of autoantibodies against MMP-7 may therefore be of particular value early in the disease process.

However, immune response and presence of autoantibodies are patient dependant (Kotera et al, (1994) Cancer Res., 54, 2856-2860; Korneeva et al., (2000) Am. J. Obs. Gynecol., 183, 18-21).

The present invention, therefore, also provides a method for aiding in the diagnosis of RCC in high risk population, comprising the steps of determining the amount of MMP-7, pro-MMP-7 and/or MMP-7 autoantibody specifically in body fluid samples obtained from the patient and comparing such measured amount to a cut-off defined by any known statistical method (95% Cl of control population or slope of ROC curve).

Presence of a significantly increased amount of MMP-7, pro-MMP-7 and/or MMP-7 autoantibody in the patient's body fluid is an indication of RCC.

The method of the present invention may also be conducted as a method for monitoring the course or progression of cancer in a patient who has been diagnosed with primary RCC.

In case of partial or total nephrectomy the method is used to measure the efficacy of chirurgical treatment, comprising carrying out periodic tests by determining the MMP-7, pro-MMP-7 and/or MMP-7 autoantibody concentration in a sample of a biological fluid from a RCC patient, wherein serum concentrations of MMP-7, pro-MMP-7 and/or MMP-7 autoantibody coming back to a basal level are indicative of treatment efficacy.

The method can also be used to measure the efficacy of immunotherapy treatment for RCC patients having metastases at initial diagnosis, comprising carrying out periodic tests by determining the MMP-7, pro-MMP-7 and/or MMP-7 autoantibody concentrations in a sample of a biological fluid from RCC patient, wherein decreasing levels of MMP-7, pro-MMP-7 and/or MMP-7 autoantibody levels are indicative of sensitivity or success of treatment.

The method can also be used to detect tumor recurrence in an RCC patient after complete remission comprising periodically measuring MMP-7, pro-MMP-7 and/or MMP-7 autoantibody levels in biological fluid from patient, wherein increased concentrations of MMP-7, pro-MMP-7 and/or MMP-7 autoantibody indicate recurrence of disease.

MMP-7, pro-MMP-7 and/or MMP-7 autoantibody can be measured alone or in combination with other routine diagnostic methods.

Combination assays of serum MMP-7, pro-MMP-7 and/or MMP-7 autoantibody and other tumor markers or diagnosis tools will be beneficial for diagnosis, monitoring evolution and follow-up of RCC.

MMP-7 and pro-MMP-7 are measured using antibodies or any specific ligand that specifically bind to human MMP-7 and pro-MMP-7, respectively.

Specific ligands represent ligands to human MMP-7, pro-MMP-7, variants or breakdown products of these enzymes which are specific for MMP-7, pro-MMP-7 and show substantially no cross-reactivity with other MMPs.

It is obvious that these ligands have no cross-reactivity to human albumin, α-globulin and hemoglobin.

The presence of MMP-7 and/or pro-MMP-7 can be measured or detected with relative ease in samples of body fluids (for example plasma, serum) using specific ligand assay techniques which are known per se. Among specific ligands there are i.e. antibodies, aptamers, oligomers. Among specific ligand assay techniques there are standard antibody-based detection systems such as immunoassays, for example sandwich assays or competitive assays, and immunoblotting techniques.

The invention relates to a method of detecting and measuring specifically MMP-7 and/or pro-MMP-7 as RCC markers, which method is a specific ligand assay technique comprising contacting a sample to be tested for the presence of such MMP-7 and/or pro-MMP-7 with an ligand assay reagent and detecting the presence of complexes formed by specific binding of the ligand assay reagent to any MMP-7 and/or pro-MMP-7 present in the sample.

The invention relates also to a method of detecting and measuring specifically autoantibodies against MMP-7 and/or pro-MMP-7 as RCC markers, which method is a specific ligand assay technique comprising contacting a sample to be tested for the presence of such autoantibodies against MMP-7 and/or pro-MMP-7 with an ligand assay reagent and detecting the presence of complexes formed by specific binding of the ligand assay reagent to any autoantibodies against MMP-7 and/or pro-MMP-7 present in the sample.

Extensive discussion of the known immunoassay techniques is not required here since these are known to those of skill in the art. Typical suitable immunoassay techniques include sandwich enzyme-linked immunoassays (ELISA), radioimmunoassays (MA), competitive binding assays, homogeneous assays, heterogeneous assays, etc. Various of the known immunoassay methods are reviewed in Methods in Enzymology (1980) 70, pp. 30-70 and 166-198. Direct and indirect labels can be used in immunoassays.

In one embodiment of the invention, the immunological reaction detection method is based on the so-called TRACE technology (Mathis, Clin Chem. (1993) 39(9), 1953-9).

The method of the invention comprises contacting serum from a RCC individual with one or several ligand(s) reactive with human MMP-7, pro-MMP-7, anti-MMP-7 antibody and/or anti-pro-MMP-7 antibody.

Preferably, the ligands to human MMP-7, pro-MMP-7 or variants are specific for MMP-7 or pro-MMP-7 and show substantially no cross-reactivity with MMPs other than MMP-7 and pro-MMP-7.

Preferably, the ligands to human anti-MMP-7 antibody and anti-pro-MMP-7 antibody are specific for anti-MMP-7 and anti-pro-MMP-7 antibodies and have substantially no cross-reactivity to other anti-MMP antibodies.

MMP-7 and pro-MMP-7 can be used as ligand for anti-MMP-7 antibody and anti-pro-MMP-7 antibody, respectively.

However, at least one ligand should be specific when the assay is performed with two or several ligands resulting in specific measurements of MMP-7 and/or pro-MMP-7.

In one embodiment, specific ligands are polyclonal and/or monoclonal antibodies to human MMP-7 and/or pro-MMP-7.

Up to date, there is no information regarding metabolism of MMP-7 and pro-MMP-7. Therefore, as for many proteins we can assume that MMP-7 and pro-MMP-7 may exist in different modified forms (i.e. post-translational modifications, mutations, degradation).

In this way, the evaluation of MMP-7 and pro-MMP-7 is intended to cover measurements which detect different forms of MMP-7 and pro-MMP-7.

The present invention provides also a kit for carrying out the above method comprising means for detecting MMP-7 and/or pro-MMP-7 in biological fluid.

Such a kit can contain all the necessary elements to perform an assay described above.

Experimental Section and Examples

Materials and Methods

Serum Samples

All serum samples were isolated from venous human blood samples taken from either patients diagnosed with renal cell carcinoma (n=177) or from normal volunteer donors (n=116) (after informed consent was given from each individual).

Immunoassays

For the determinations described below both a commercially available immunoassay kit, Human MMP-7 Quantikine ELISA Kit (DMP700) (R&D Systems Europe Ltd. Abingdon UK) and a homogeneous MMP-7 immunoassay based on the TRACE technology (Mathis, Clin Chem. 39(9), 1953-9 (1993)), were used.

a) Human MMP-7 Enzyme-Linked Immunoassay

The assay employs the quantitative sandwich enzyme immunoassay technique. A monoclonal antibody specific for MMP-7 has been pre-coated onto a microplate. Standards and samples are pipetted into the wells, and MMP-7 is bound by the immobilized antibody. After washing away unbound substances, an enzyme-linked polyclonal antibody specific for MMP-7 is added to the wells. Following a wash to remove unbound antibody-enzyme reagent, a substrate solution is added to the wells and color develops in proportion to the amount of total MMP-7 (pro and/or active) bound in the initial step. The color development is stopped and the intensity of the color is measured at 450 nm wavelength absorbance by FLUOstar microplate reader (BMG Labtechnologies, GmbH, Offenburg, Germany).

The assay was performed according to the manufacturer R&D Systems' prescribed assay protocol.

b) Human MMP-7 Homogenous Immunoassay Based on TRACE Technology (Mathis, Clin Chem. 39(9), 1953-9 (1993))

The assay employs TRACE (Time Resolved Amplified Cryptate Emission) technology, based on a non-radiative transfer of energy. This transfer takes place between two fluorescent tracers:—a donor: europium cryptate,—an acceptor: AF647.

In the assay, they are each bound to a monoclonal antibody specific for human MMP-7. After excitation, the cryptate emits a long life fluorescent signal at 620 nm. AF647 emits a signal at 665 nm which has a short life except when it is excited by a transfer of energy from cryptate. This transfer depends on the proximity of donor to acceptor in the immunological complex, as well as on the recovery of the donor's emission spectrum and of the acceptor's absorption spectrum. The signal measured during the formation of the antigen-antibody complex is accompanied by an amplification. The specific fluorescence (RFU) which is proportional to the antigen concentration is obtained through a double selection: spectral (separation depending on wave-length) and temporal (time resolved measurement). This assay is homogeneous, without separation or washing. The molecules of MMP-7 present in the assay samples are sandwiched between two monoclonal antibodies specific for human MMP-7 (Cezanne SAS, France). The intensity of the signal (RFU) is proportional to the amount of MMP-7.

In the assay, two monoclonal anti-human MMP-7 antibodies were coupled to AF647 fluorophore (Molecular Probes, Inc., Eugene, Oreg.) and to europium cryptate TBP-mono-MP (Schering AG GmbH, Germany), respectively. The coupling reactions were performed according to the manufacturer prescribed coupling protocols.

The stock AF647-conjugated antibody and cryptate-conjugated antibody solutions were diluted at 5 μg/ml and 0.35 μg/ml with assay buffer (0.1M sodium phosphate, pH 7.1, 0.1% BSA free protease, 0.6 M KF, 0.2 mg/ml mouse IgG), respectively, prior to use.

Measurements and Results a) Standard Curve and Measurement of MMP-7 Levels in Serum of Patients with Renal Cell Carcinoma (RCC) Using Enzyme-Linked Immunoassay Technique The standard curve was obtained using the recombinant human MMP-7 (Quantikine kit standards). The recombinant human MMP-7 was diluted in calibrator diluent RD6-28 (Quantikine kit) to give MMP-7 standard values of 0.156, 0.312, 0.625, 1.25, 2.5, 5, and 10 ng/ml.

Serum samples with >10 ng/ml of MMP-7 concentration were diluted with calibrator diluent RD6-28 (Quantikine kit) to produce samples with values within the dynamic range of the assay.

Standards or serum samples (50 μL) and assay diluent (100 μl) were added to the wells of microtiter plate. After incubation for 2 hours at room temperature on a horizontal orbital shaker, each well was washed 4 times with wash buffer (400 μl). 200 μl of MMP-7 conjugate were added to each well, followed by incubation of microtiter plate for 2 hours at room temperature on the shaker. After 4 washing steps and addition of substrate solution (200 μl) to each well, microplate was incubated for 30 minutes at room temperature. The reaction was stopped with stop solution (50 μl) and the optical density of each well was determined using FLUOstar microplate reader to 450 nm.

Normal human sera (n=116) were used as control samples. The standard curve is shown in FIG. 1.

Figure 2:
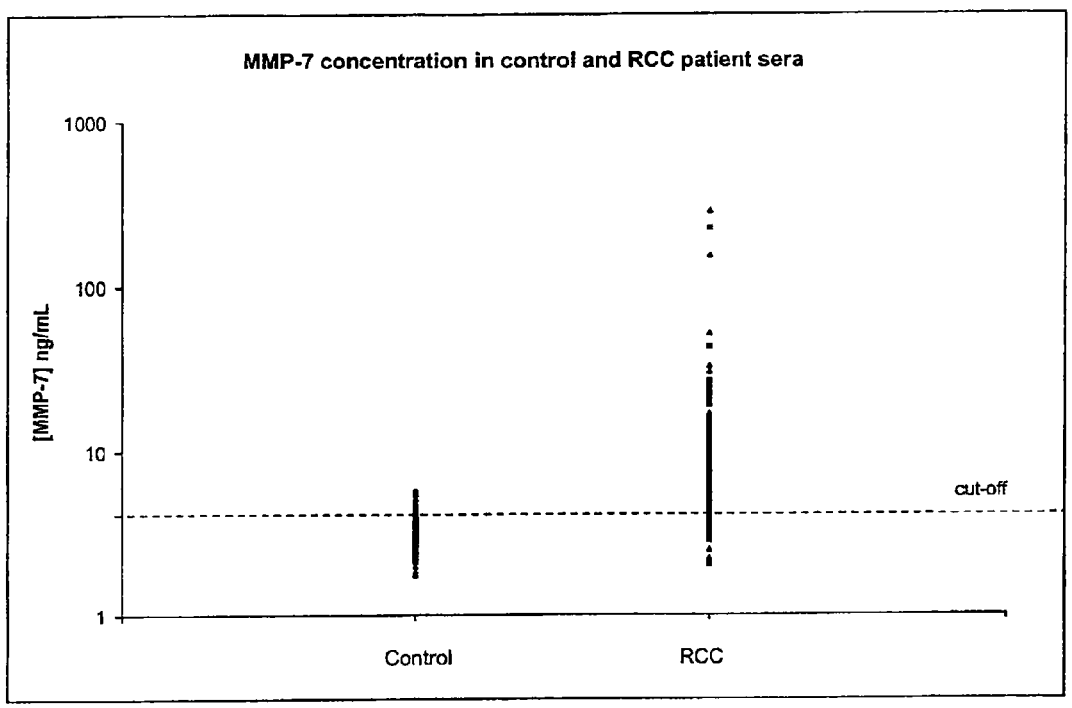
FIG. 2 is a diagrammatic representation of the results of measurements of MMP-7 in sera of RCC patients and healthy controls with an enzyme-linked immunoassay as described in the experimental section.

RCC patients had increased serum MMP-7 levels compared to control subjects (Table 1 and FIG. 2).

TABLE 1

| Groups | n | Mean ± SD | Sensitivity (cut-off 4.78 ng/ml) | Specificity (cut-off 4.78 ng/ml) |
|---|---|---|---|---|
| RCC | 177 | 12.59 ± 29.13 ng/ml | 79.7% | 95% |
| Control | 116 | 3.27 ± 0.83 ng/ml | | |

In Table 1:
Sensitivity = True-positive/True-positive + False-negative;
Specificity = True-negative/True-negative + False-positive b) Standard Curve and Measurement of MMP-7 Levels in Serum of Patients with Renal Cell Carcinoma (RCC) Using Trace Technology The standard curve was obtained using cell culture supernatant of Cal-54 cell line (DSMZ, GmbH, Germany) established from human kidney carcinoma (Gioanni et al., Bull Cancer 83: 553 (1996)). The culture supernatant containing natural MMP-7 was diluted in newborn calf serum (NBCS) to give MMP-7 standard values of 1, 2, 4, 6.1, 9, 9.9, 16.3 and 42.8 ng/ml. The standards were calibrated against highly purified recombinant human MMP-7 (R&D Systems Europe Ltd. Abingdon UK). NBCS was used as zero standard. Normal human sera (n=61) were used as control samples.

Serum samples with >42.8 ng/ml of MMP-7 concentration were diluted with NBCS to produce samples with values within the dynamic range of the assay.

Standards and samples (50 μl) were placed in a tube suitable for use on BRAHMS Kryptor automate (12-13 mm diameter), followed by addition of the AF647-conjugated antibody (50 μl) and cryptate-conjugated antibody (50 μl) solutions prepared as described in "Materials and methods" (b). After incubation at 37° C. during 1 hour, specific fluorescence (RFU) was measured by simultaneous dual wavelength measurement at 665 and 620 nm using BRAHMS Kryptor automate (BRAHMS Aktiengesellschaft, Hennigsdorf, Germany).

Figure 4:
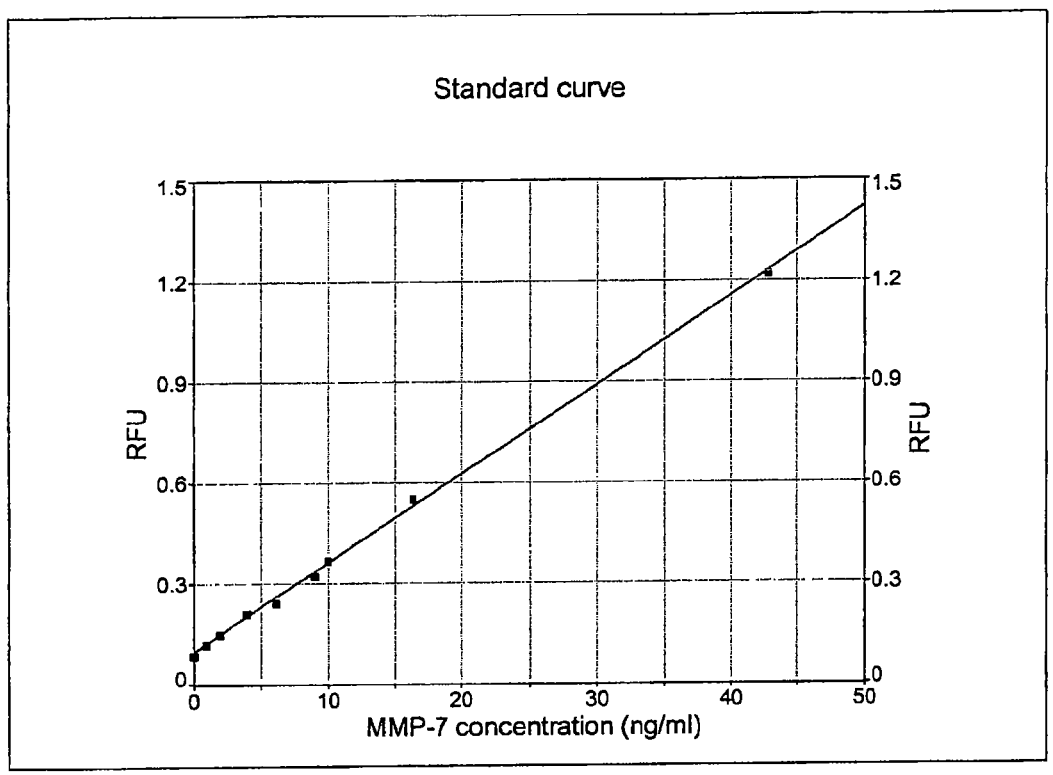
FIG. 4 is a standard curve for the measurement of MMP-7 levels in serum of patients with renal cell carcinoma (RCC) with a homogeneous immunoassay based on the TRACE technology as described in the experimental section.

The standard curve is shown in FIG. 4.

Figure 5:
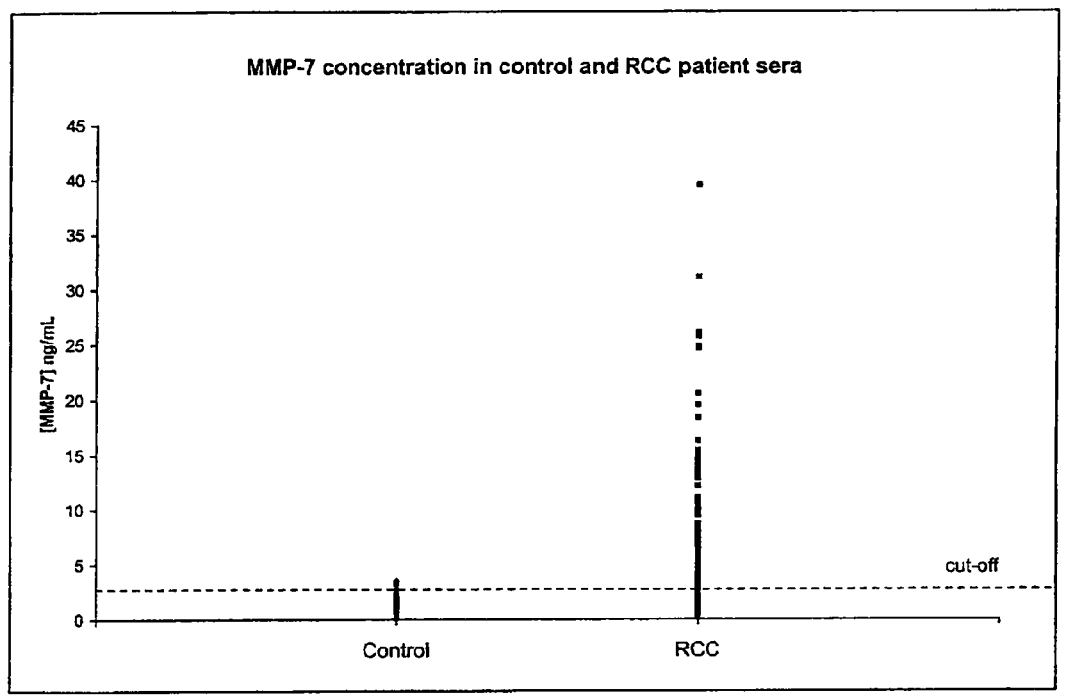
FIG. 5 is a diagrammatic representation of the results of measurements of MMP-7 in sera of RCC patients and healthy controls with a homogeneous immunoassay based on the TRACE technology as described in the experimental section.

RCC patients had increased serum MMP-7 levels compared to control subjects (Table 2 and FIG. 5).

TABLE 2

| Groups | n | Mean ± SD | Sensitivity (cut-off 3.37 ng/ml) | Specificity (cut-off 3.37 ng/ml) |
|---|---|---|---|---|
| RCC | 100 | 13.51 ± 42.32 ng/ml | 79% | 95% |
| Control | 61 | 1.58 ± 0.97 ng/ml | | |

In Table 2:
Sensitivity = True-positive/True-positive + False-negative;
Specificity = True-negative/True-negative + False-positive b) Statistical Analysis and ROC Curve.

The clinical sensitivity versus clinical specificity diagram is presented by ROC (Receiver-Operating Characteristics) curve.

For calculations of clinical sensitivity and clinical specificity, 95% confidence intervals were determined based on the binomial distribution (Besnard et Morin, In: Immunostat, Paris, Edition Nucléon, 227-251 (1997)).

If we consider the cut-off of the assay used in the experiments as being at 4.78 ng/ml (MMP-7 Quantikine ELISA kit) and 3.37 ng/ml (MMP-7 immunoassay based on TRACE technology) defined by maximal orthogonal distance between ROC curve and diagonal, the clinical sensitivity of the MMP-7 determination in RCC is 79% (see Table 1 and Table 2).

Figure 3:
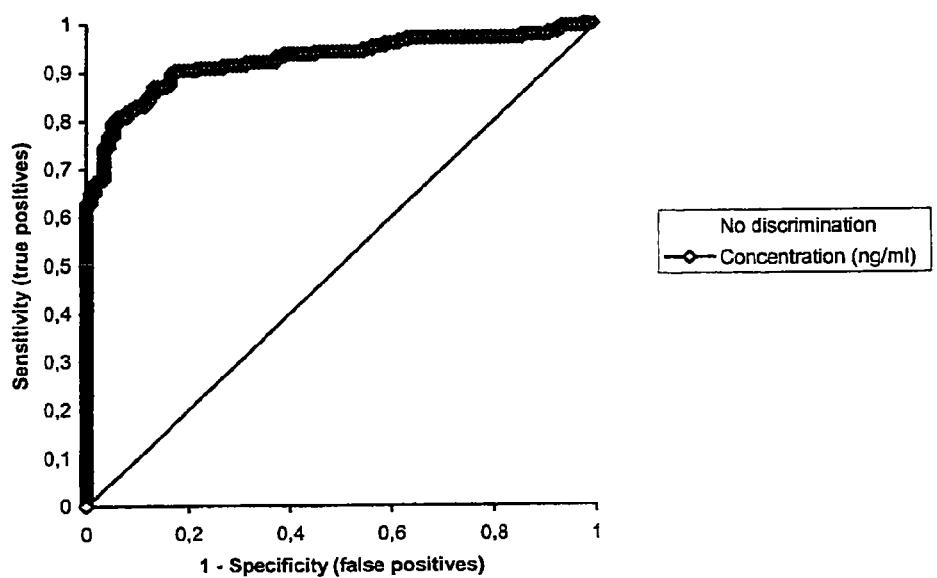
FIG. 3 is a ROC (Receiver-Operating Characteristics) curve indicative for the clinial diagnostic validity (sensitivity vs. specifity) of the determination of increased MMP-7 levels in sera of RCC patients with an MMP-7 Quantikine ELISA kit.
Figure 6:
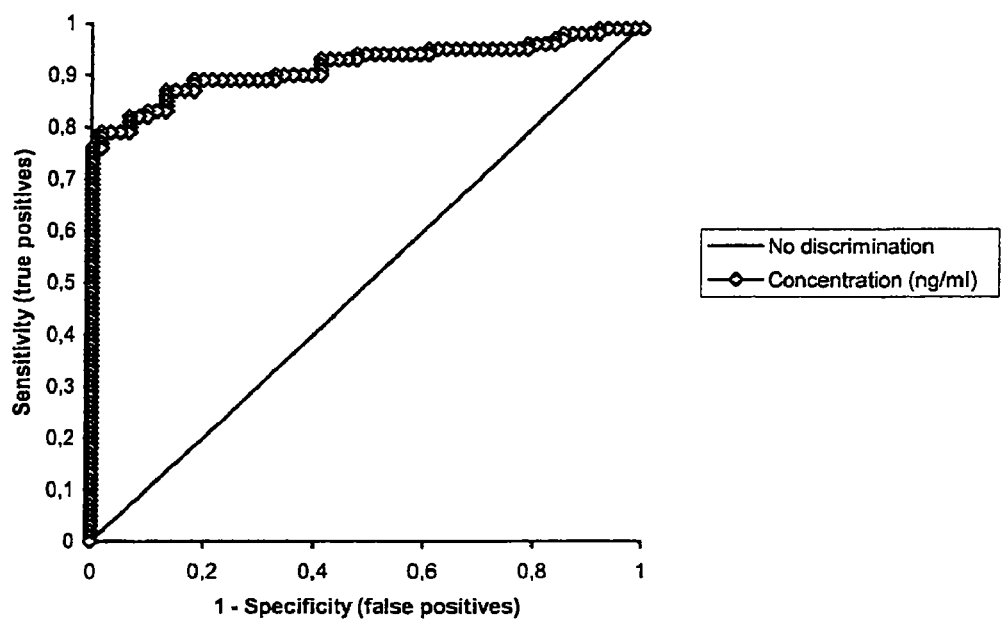
FIG. 6 is a ROC (Receiver-Operating Characteristics) curve indicative for the clinical diagnostic validity (sensitivity vs. specificity) of the determination of increased MMP-7 levels in sera of RCC patients with homogeneous immunoassay based on TRACE technology.

The ROC curves are shown in FIG. 3 and FIG. 6.

The invention claimed is:

1. An in vitro method for diagnosing renal cell carcinoma (RCC) in a human patient, said method comprising:
    obtaining from a human patient suspected of having renal cell carcinoma (RCC) a sample selected from a blood, serum and plasma sample;
    contacting said sample with first and second antibodies that specifically bind to matrix metalloproteinase 7 (MMP-7);
    determining in said sample the level of MMP-7 and/or its pro-enzyme form (pro-MMP-7); and
    associating the level of MMP-7 and/or pro-MMP-7 with the presence of RCC in said human patient if the level is increased compared to levels found in normal human individuals.

2. The method of claim 1, further comprising measuring the levels of MMP-7 in a body fluid of a patient at consecutive time intervals.

3. The method of claim 2, wherein said method is conducted as a method for measuring the efficacy of a treatment of RCC, wherein a decrease in the levels of MMP-7 between measurements is indicative of the efficacy of the treatment.

4. The method of claim 1, wherein the measured MMP-7 can be attributed to the presence of MMP-7 itself and/or of its proenzyme form (pro-MMP-7).

5. The method of claim 1, wherein a concentration ≧3.37 ng/ml of MMP-7 and/or pro-MMP-7 is indicative of RCC.

6. The method of claim 1, wherein a concentration of ≧4.78 ng/ml of MMP-7 and/or pro-MMP-7 is indicative of RCC.

* * * * *